(12) United States Patent
Smith, Jr.

(10) Patent No.: US 7,086,484 B2
(45) Date of Patent: Aug. 8, 2006

(54) DETERMINATION OF THERMAL PROPERTIES OF A FORMATION

(75) Inventor: Harry D. Smith, Jr., Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 223 days.

(21) Appl. No.: 10/457,645

(22) Filed: Jun. 9, 2003

(65) Prior Publication Data
US 2004/0244970 A1 Dec. 9, 2004

(51) Int. Cl.
*E21B 47/06* (2006.01)
(52) U.S. Cl. .......................... 175/50; 175/11; 175/12; 166/250.01; 73/152.12; 73/152.13
(58) Field of Classification Search ............... 175/11, 175/16, 12, 40, 45, 50; 73/152.13, 152.12; 166/250.01
See application file for complete search history.

(56) References Cited

U.S. PATENT DOCUMENTS

| | | | |
|---|---|---|---|
| 3,126,959 A | | 3/1964 | Ortloff |
| 3,807,227 A | | 4/1974 | Smith, Jr. |
| 3,864,969 A | | 2/1975 | Smith, Jr. |
| 3,871,485 A | * | 3/1975 | Keenan, Jr. .................. 175/16 |
| 3,892,128 A | | 7/1975 | Smith, Jr. |
| 3,905,010 A | * | 9/1975 | Fitzpatrick ............... 340/854.4 |
| 3,935,910 A | | 2/1976 | Gaudy et al. |
| 4,199,034 A | * | 4/1980 | Salisbury et al. ............. 175/11 |
| 4,313,342 A | | 2/1982 | Poppendiek |
| 4,343,181 A | | 8/1982 | Poppendiek |
| 4,375,164 A | * | 3/1983 | Dodge et al. ............. 73/152.12 |
| 5,010,764 A | * | 4/1991 | Taylor ..................... 73/152.52 |
| 5,168,940 A | | 12/1992 | Foppe |
| 5,735,355 A | | 4/1998 | Bussod et al. |
| 5,771,984 A | | 6/1998 | Potter et al. |
| 6,112,809 A | * | 9/2000 | Angle ......................... 166/66 |
| 6,618,677 B1 | * | 9/2003 | Brown ........................ 702/13 |

OTHER PUBLICATIONS

Alexandre, Isabelle, "Fiber-Optic Temperature Measurement" (Retrieved from the Internet on Aug. 14, 2002 at URL: http://www.sensorsmag.com/articles/0501/57/main.shtml; pp. 1-3.

Freudenrich, Craig C., Ph.D., "How Fiber Optics Work" (Retrieved from the Internet on Aug. 14, 2002 at URL: http://www.howstuffworks.com/fiber-optic.htm/printable; pp. 1-10.

O'Brien, Darien G., et al, "Lasers May Revolutionize Drilling & Completions in the 21st Century," *GasTIPS*, Feb. 1999 (Retrieved from the Internet on May 17, 2002 at URL: http://www.gastechnology.org/pub/content/feb/19990218/125839/; 15 pp.

(Continued)

*Primary Examiner*—David Bagnell
*Assistant Examiner*—G M Collins
(74) *Attorney, Agent, or Firm*—Conley Rose, P.C.

(57) ABSTRACT

The present invention relates to methods and apparatus for making in situ thermal property determinations utilizing a heat source employed in wellbore stabilization procedures, well drilling, or well perforating, for example. In particular, using a heat source, such as a laser driller, to enable formation temperature measurements. Based on these measurements, thermal properties of the formation may be inferred.

22 Claims, 7 Drawing Sheets

OTHER PUBLICATIONS

Parker, Richard, "Lasers May Bring Science Fiction Down to Earth for Gas Drilling," *GRID Magazine*, Dec. 1998 (Retrieved from the Internet on May 17, 2002 at URL: http://www.gastechnology.org/pub/content/sep/19990923/144419/wteplaser22.html; pp. 1-2.

"Laser Drilling," Retrieved from the Internet on May 17, 2002 at URL: http://www.gastechnology.org/pub/solutions/starwars/; pp. 1-2.

Burkhardt, H. et al, "Test measurements with a new thermal conductivity borehole tool," *Tectonophysics* 244 (1995), pp. 161-165.

Chlew, Yee C. et al, "Simultaneous Conduction and Radiation in Porous and Composite Materials: Effective Thermal Conductivity," *Ind. Eng. Chem. Fundam.* 1983, vol. 22, No. 3, pp. 276-282.

Dove, R.E. et al. "Thermal Conductivity Estimated from Elemental Concentration Logs," *Nucl. Geophys*, 1989, vol. 2, No. 2, pp. 107-112.

Figueroa, H. et al, "Rock removal using high power lasers for petroleum exploitation purposes," 13 pp.

Förster, Andea et al, "Prediction of Thermal Conductivity from Wireline Log Measurements in Midcontinent Paleozoic Rocks," Jun. 4, 1997, 1 page.

Hoang, Viet T. et al, "Effect of Variable Thermal Conductivity of the Formations on the Fluid Temperature Distribution in the Wellbore," SPWLA Twenty-Second Annual Logging Symposium, Jun. 23-26, 1981, pp. 1-24.

Kersey, Alan D. et al, "A Continuous Stream," *Hart's E & P*, Oct. 1999, pp. 141, 142, 144, 146, and 148.

Kersey, Alan D. "Fiber Optic Sensors: An Introduction for Engineers and Scientists," *John Wiley & Sons, Inc.*, 1991, Chapter 11, pp. 327-329, 333-335, 366.

Lee, Tien-Chang, "Estimation of Formation Temperature and Thermal Property from Dissipation of Heat Generated by Drilling," *Geophysics*, Nov. 1982, vol. 47, No. 11, pp. 1577-1584.

Poulsen, Kurt D., et al, "Thermal Conductivity Measurements on Silurian Limestones from the Island of Gotland, Sweden," *GFF* 1981, vol. 103, pp. 349-356.

Rybach, L., et al, "Sediment Thermal Conductivity Derived from Wireline Logs—Calibration by Cores and Cuttings," EAGE 59th Conference and Technical Exhibition, Geneva, Switzerland, May 26-30, 1997, 2 pp.

Somerton, Wilbur H., et al, "Ring Heat Source Probe for Rapid Determination of Thermal Conductivity of Rocks," *The Review of Scientific Instruments*, Oct. 1967, vol. 38, No. 10, pp. 1368-1371.

Williams, Colin F., et al, "In SITU Investigations of Thermal Conductivity, Heat Production, and Past Hydrothermal Circulation in the Cajon Pass Scientific Drillhole, California," *Geophysical Research Letters*, Aug. Supplement 1988, vol. 15, No. 9, pp. 985-988.

Xu, Hui, et al, "Formation Evaluation Using In-Situ Measurements of Formation Thermal Properties," SPWLA 31st Annual Logging Symposium, Jun. 24-27, 1990, pp. 1-25.

Yamada, S.E., "A Transient Technique for *In-situ* Thermal Property Measurements," *Int. J. Rock Mech. Min. Sci. & Geomech. Abstr.* 1982, vol. 19, pp. 149-152.

Zishun, Li, et al "Detect Oil and Gas by Heat-Conduction Logging Techniques," SEG International Exposition and 72nd Annual Meeting, Oct. 7-9, 2002, 4 pp.

"Thermal Boring—Progress at LASL," *Nuclear News*, Feb. 1972, p. 47.

Anand, J., et al, "Predicting Thermal Conductivities of Formations From Other Known Properties," *Society of Petroleum Engineers Journal*, Paper SPE 4171, Oct. 1973, pp. 267-273.

International Search Report and Written Opinion, PCT/US04/17834, Jul. 7, 2005, 13 pgs.

Brown, G.A., et al, "Using Fibre-Optic Distributed Temperature Measurements to Provide Real-Time Reservoir Surveillance Data on Wytch Farm Field Horizontal Extended-Reach Wells," Society of Petroleum Engineers, Paper SPE 62952, Oct. 1-4, 2000, pp. 1-11.

Carnahan, B.D., et al, "Fiber Optic Temperature Monitoring Technology," Society of Petroleum Engineers, Paper SPE 54599, May 26-28, 1999, pp. 1-10.

Gahan, Brian C., et al, "Laser Drilling: Determination of Energy Required to Remove Rock," Society of Petroleum Engineers, Paper SPE 71466, Sep. 30, 2001 to Oct. 3, 2001, pp. 1-11.

Gomaa, Ezzat E., et al, "Thermal Behavior of Multifluid-Saturated Formations Part II: Effect of Vapor Saturation—Heat Pipe Concept and Apparent Thermal Conductivity," Society of Petroleum Engineers of AIME, Paper SPE 4896-B, Apr. 4-5, 1974, pp. 1-12.

Graves, Ramona M., et al, "Temperatures Induced by High Power Lasers: Effects on Reservoir Rock Strength and Mechanical Properties," Society of Petroleum Engineers, Paper SPE/ISRM 78154, Oct. 20-23, 2002, pp. 1-7.

Hasan, A.R., et al, "Heat Transfer During Two-Phase Flow in Wellbores: Part 1—Formation Temperature," Society of Petroleum Engineers, Paper SPE 22866, Oct. 6-9, 1991, pp. 469-478.

O'Brien, D.G., et al, "StarWars Laser Technology for Gas Drilling and Completions in the 21st Century," Society of Petroleum Engineers, Paper SPE 56625, Oct. 3-6, 1999, pp. 1-10.

O'Dell, Mike, "Find Thermal Diffusivity from Temperature Surveys," Society of Petroleum Engineers, Paper SPE 35738, May 22-24, 1996, pp. 711-712.

Seto, A.C., "Thermal Conductivity Estimation from Temperature Logs," Society of Petroleum Engineers, Paper SPE 21542, Feb. 7-8, 1991, pp. 179-186.

* cited by examiner

DETERMINATION OF THERMAL PROPERTIES OF A FORMATION

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND

1. Field of the Invention

The present invention relates to the evaluation of downhole formations from the in situ determination of thermal properties. More particularly, the present invention relates to the in situ determination of thermal properties, such as specific heat, thermal conductivity, and thermal diffusivity from wellbore temperature measurements. Still more particularly, the present invention relates to the in situ determination of thermal properties performed while utilizing a heat source employed in wellbore stabilization, drilling, or perforating.

2. Description of the Related Art

Modern petroleum drilling and production operations demand a great quantity of information relating to parameters and conditions downhole. Such information typically includes the characteristics of the earth formations traversed by the wellbore, and the location of subsurface reservoirs of oil and gas. Samples of the formation and reservoir may be retrieved to the surface for laboratory analysis. However, to enhance drilling and production operations, it is much more valuable to provide real-time access to the data regarding downhole conditions. Thus, it has become commonplace to make in situ measurements of many formation properties via wellbore logging tools, such as logging-while-drilling (LWD) and wireline tools, that may be operated by electromagnetic, acoustic, nuclear or electromechanical means, for example. These logging tools enable in situ determinations of such properties as the porosity, permeability, and lithology of the rock formations; reservoir pressure and temperature in the zones of interest; identification of the fluids present; and many other parameters.

It has been suggested that thermal properties of the formation, such as thermal diffusivity, thermal conductivity, and specific heat (or specific heat capacity), are valuable for determining rock and fluid properties. Thermal diffusivity enables a determination of rock characteristics, such as whether the formation comprises sand, limestone, shale, or granite, for example. Specific heat enables a determination of fluid properties, such as whether the formation is saturated with hydrocarbons or water. In particular, the specific heat of water is approximately twice the specific heat of a hydrocarbon, regardless of whether the hydrocarbon is a liquid or gas. Thermal conductivity enables further differentiation between liquid and gas hydrocarbon-saturated formations. In particular, the thermal conductivity of a water-saturated formation is approximately twice the thermal conductivity of an oil-saturated formation, and the thermal conductivity of an oil-saturated formation is approximately twice the thermal conductivity of a gas-saturated formation.

Thermal conductivity (K), the physical property of a material that determines how easily heat can pass through it, is defined by equation (1), which relates several thermal properties as follows:

$$K = \rho \cdot C \cdot \kappa \quad (1)$$

where $\rho$ is the material density, $C$ is the specific heat capacity, and $K$ is the thermal diffusivity. Specific heat capacity (C) is defined as the quantity of heat required to raise the temperature of one unit of mass of material by one temperature degree. Thus, the units of specific heat capacity (C) may be calorie/gram° C., for example. Thermal diffusivity ($\kappa$) is defined as the rate at which heat is conducted during unsteady state heat transfer.

To make thermal property determinations, the most common method is to take a sample of the formation downhole, retrieve it to the surface, and then evaluate the sample in a laboratory. The laboratory method does not enable real-time data acquisition, and can only be accurate with respect to the particular sample acquired. Since formation properties typically change with depth, it is likely that the laboratory analysis will not provide complete data for all zones of the formation. Other methods include inferring thermal properties from ambient borehole temperatures measured by conventional wellbore logging tools. This method has some limitations, including the inability to make accurate measurements through casing to determine formation properties behind the casing and the cement that surrounds it.

Yet another known method for determining thermal properties is to provide downhole a constant output heat source and to measure the temperature relaxation over time, which enables accurate measurements in both cased and uncased boreholes. U.S. Pat. No. 3,807,227 ('227 patent) and U.S. Pat. No. 3,892,128 ('128 patent) to Smith, Jr. disclose such thermal well logging methods for determining specific heat and thermal conductivity, respectively. A single heat source and preferably three spacially separated thermal detectors are disposed on a well logging tool that is moved vertically through a borehole while the thermal responses are recorded. In particular, one thermal detector measures ambient temperature of the borehole at a particular depth before the heat source passes that depth. The other two thermal detectors measure the temperature of the borehole at the same depth following the heat source, each at a different time. In one embodiment, the heat source is disclosed to be a heat drilling tip that melts the earth formations to produce a borehole. Examples of modern heat drilling tips are disclosed in U.S. Pat. No. 5,735,355 to Bussod et al. comprising a rock melting tool with an annealing afterbody that cools the molten rock, and U.S. Pat. No. 5,771,884 to Potter et al comprising a spallation head with rotating, circumferentially spaced jets that dispense flame jets, very hot water, and/or air to spall the formation rock, or fuse the formation rock if spallation is not feasible.

The '227 patent discloses that in a borehole environment, the change in temperature ($\Delta T$) is related to the radiated energy (Q) from the heat source, the mass of the heated earth formation (M) and its composite specific heat (C) as given by the relationship of equation (2):

$$Q = C \times M \times \Delta T \quad (2)$$

Similarly, the '128 patent discloses that thermal conductivity (K) is proportional to the time rate of heat transfer in the formation. The one dimensional relationship governing the energy transfer ($\Delta Q$) during a short period of time ($\Delta t$) in a formation having a temperature differential ($\Delta T$) over a length ($\Delta X$) is given by Equation (3):

$$\frac{\Delta Q}{\Delta t} = K \times \alpha \times \frac{\Delta T}{\Delta X} \quad (3)$$

where $\alpha$ is a constant dependent on the geometry of the borehole, the formation, and the well logging tool; and K is thermal conductivity. Thus, according to the '227 patent and the '128 patent, the specific heat (C) and the thermal conductivity (K) of the formation can be inferred using equation (2) and equation (3), respectively, based on temperature measurements. Using these inferred values, qualitative evaluations of likely locations of water and hydrocarbon deposits can be made.

U.S. Pat. No. 3,864,969 ('969 patent) to Smith, Jr. discloses two methods for determining thermal conductivity (K) of the formation by heating one spot within the formation. In the first method, the formation is heated for a predetermined length of time to elevate the temperature. Then the heat source is removed and the rate of temperature decay is measured over time until the formation returns to ambient temperature. In the second method, the formation is heated by a constant output heat source and the formation's rate of temperature increase is measured to derive an indication of thermal conductivity (K).

Similarly, U.S. Pat. No. 4,343,181 (the '181 patent) to Poppendiek discloses a method for in situ determinations of the thermal conductivity and thermal capacity per unit volume of the earth. The '181 patent teaches a probe containing a heater and two temperature sensors spacially displaced from one another. The probe is positioned in the borehole at the level of interest and maintained at that position for a period sufficient for the probe to be in thermal equilibrium with its surroundings. The probe is displaced from the borehole wall by a thin fluid annulus, and it is not in contact with the borehole wall. The thermal gradient between the two temperature sensors is recorded without heat being applied. Then, the heater is turned on to apply heat at a constant rate, and the thermal gradient between the temperature sensors is recorded. The thermal conductivity and thermal capacity per unit volume of the surrounding earth is determined by relating the actual temperature curve to a calculated theoretical curve by best-fit mathematical methods. At short times, the thermal capacity is said to dominate the temperature response curve, and at long times, the thermal conductivity is said to dominate.

Each of these prior in situ methods proposes utilizing a downhole heat source that is provided for the sole purpose of taking thermal measurements. Although this approach is technically sufficient, and valuable formation characteristics can be determined using this methodology, this approach has largely been ignored in practice. One possible explanation is that operators are not willing to incur additional capital and operating costs for a heat source that is provided solely for thermal property measurements. Thus, most commercial downhole systems do not include heat sources that enable in situ measurements of thermal properties. Accordingly, at the present time, thermal property measurements are almost exclusively restricted to analysis of samples in laboratories.

Further, although the '128 patent and the '227 patent mention the concept of a heat drilling tip that may also be used as a heat source for enabling in situ determinations of thermal properties, such heat drilling tips have proven to be too slow for commercial success. In particular, the heat drilling tip is designed to spall or actually melt the rock of the formation as the method of forming a borehole. However, because rock is very slow to spall or melt utilizing such techniques, the heat drilling tip progresses at only 3–6 feet per hour. Therefore, the heat tip has not achieved commercial recognition or success as a viable drilling alternative.

The present invention overcomes the deficiencies of the prior art by providing a convenient in situ method of measuring formation thermal properties, such as specific heat, thermal conductivity, and thermal diffusivity. The method is suitable at multiple depths using a commercially viable heat source provided downhole for wellbore stabilization, well drilling or well perforating.

SUMMARY

The preferred embodiments of the present invention feature apparatus and methods for making in situ thermal property determinations utilizing a downhole heat source that may also be employed for wellbore stabilization, well drilling, or well perforating. Temperature measurements are downhole, and thermal properties of the formation may be inferred from these measurements using conventional formulas.

Thus, the preferred embodiments of the present invention comprise a combination of features and advantages that overcome various problems of prior methods and apparatus. The various characteristics described above, as well as other features, will be readily apparent to those skilled in the art upon reading the following detailed description of the embodiments of the invention, and by referring to the accompanying drawings.

BRIEF DESCRIPTION OF THE DRAWINGS

For a more detailed description of the embodiments of the present invention, reference will now made to the accompanying drawings, in which like elements have been given like numerals, wherein.

DETAILED DESCRIPTION

Laser technology has flourished in recent years, largely through the expansion of atomic physics, the invention of fiber optics, and advances in military defense capabilities. Through these efforts, tremendous advances have occurred, for example, in laser power generation, efficiency and transmission capabilities. Improvements in lasers and other thermal technologies have made it possible to perform wellbore operations, such as wellbore stabilization, drilling, and perforating, utilizing new techniques. Because thermal technologies offer significant advantages over conventional methods, they are gaining rapid acceptance in the petroleum industry.

Lasers and other thermal technologies provide a heat source downhole to perform a primary function, such as wellbore stabilization, drilling, or perforating through casing. The heat source may also be utilized for the secondary but important purpose of determining thermal properties of the formation. Accordingly, measurements can be made of the temperature response of a borehole after it is heated by a heat source. The temperature measurements are then utilized to infer thermal properties, such as thermal conductivity, thermal diffusivity, and specific heat, according to conventional calculations.

Figure 1:
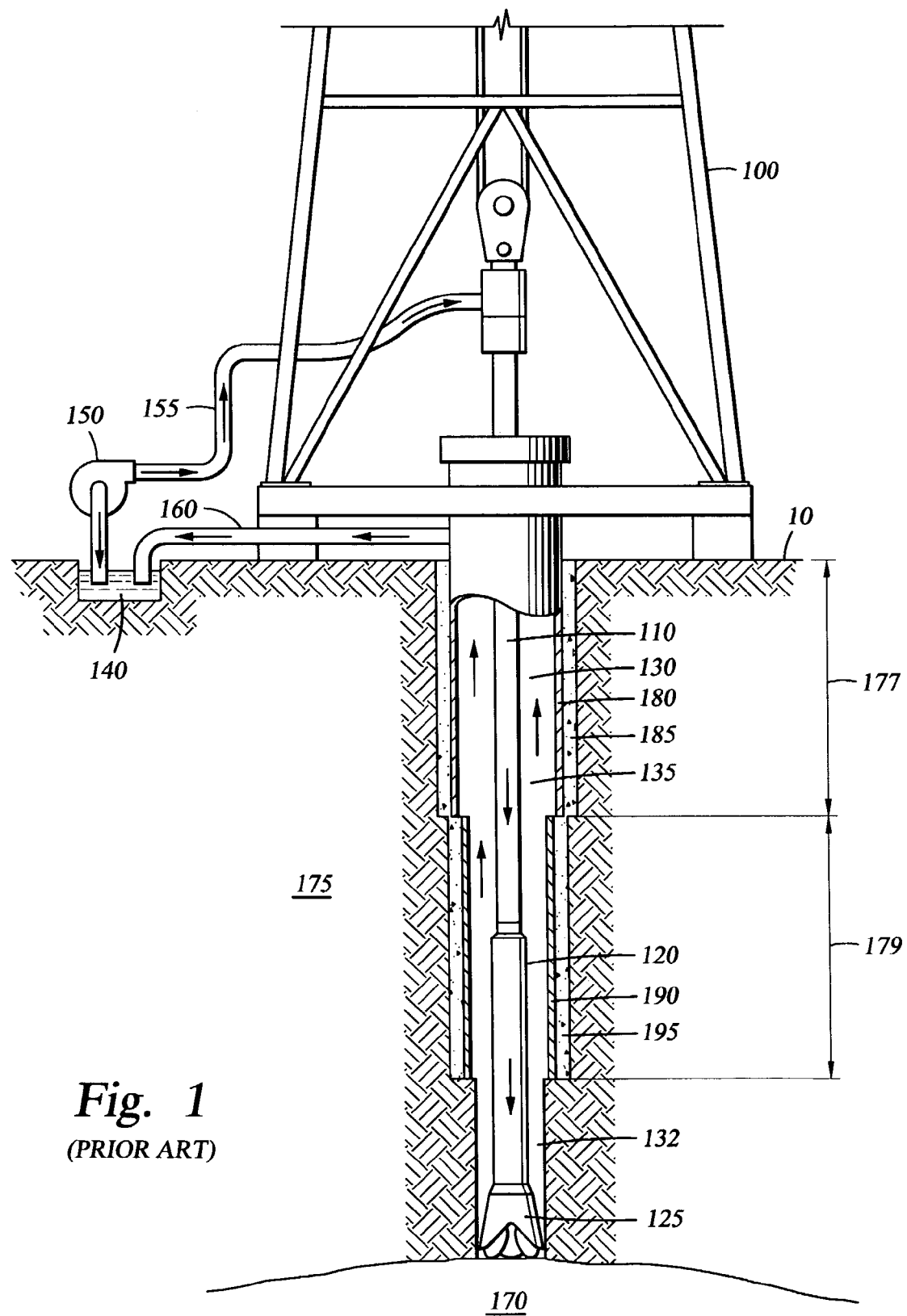
FIG. 1 is a schematic of an exemplary conventional drilling system.

Some of the perceived advantages of using lasers or other thermal technologies stem from problems encountered with conventional drilling methods. Thus, referring initially to FIG. 1, there is depicted a conventional rotary drilling operation, which comprises mainly three steps: drilling, casing, and completion. To drill a well in the conventional manner, a drilling rig 100 on the earth's surface 10 conveys a drillstring 110 and a drilling assembly 120 with a drill bit 125 on its lower end into a wellbore 130, forming an annular flow area 135 between the drillstring 110 and the wellbore 130. The drillstring 110 is rotated from the surface 10 by the drilling rig 100 while a dense fluid, known as "drilling fluid", is drawn from a reservoir 140 by a pump 150 on the surface 10. The pump 150 discharges the drilling fluid through pump discharge line 155 into the drillstring 110, downwardly into the drilling assembly 120 as depicted by the flow arrows to power the drill bit 125 and to remove the cuttings from the wellbore 130. The drilling fluid exits the drill bit 125 and returns to the surface 10 through the wellbore annulus 135. After reaching the surface 10, the drilling fluid is cleaned and returned to the reservoir 140 via the pump return line 160. Thus, the drilling fluid, which contains suspended drill cuttings, flows continuously through the drillstring 110 downwardly to the bottom of the wellbore 130 and upwardly through the wellbore annulus 135 back to the fluid reservoir 140 while removing cuttings (debris) from the wellbore 130. During drilling, the density of the drilling fluid, commonly referred to as the "mud weight", is optimized to counterbalance the earth's fluid pressure in the formation 175, thereby preventing the uncontrolled flow of fluids from the formation 175 into the wellbore 130, or preventing the drilling fluid from fracturing and flowing into the formation 175. The earth's fluid pressure is caused by the presence of water, crude oil, and pressurized gas such as $CO_2$, $H_2S$, and natural gas, within the formation 175.

In more detail, as the wellbore 130 is drilled, the mud weight may be varied from one formation zone to another to counterbalance the pressure of the formation 175. For example, if the lower zone 179 of the formation 175 is overpressured, the mud weight must be increased when drilling through zone 179 to balance the formation pressure. However, by using a heavier mud weight in the wellbore 130, the upper zone 177 of the formation 175 could be fractured if that zone 177 is underpressured. In contrast, if the lower zone 179 is underpressured, the mud weight must be decreased when drilling through zone 179 to balance the formation pressure. However, by using a lighter mud weight in the wellbore 130, a blow-out may occur in the upper zone 177 of the formation 175 if that zone 177 is overpressured. Therefore, before drilling into the lower zone 179 with a different mud weight, a steel tubular known as "casing", such as casing 180, is installed to line the wellbore 130 in the upper zone 177, thereby isolating that section of the wellbore 130 from the surrounding formation 175. The casing 180 is then cemented 185 against the formation 175 to protect fresh water supplies and other nonhydrocarbon fluids from contamination, and to provide zonal isolation between hydrocarbon and non-hydrocarbon bearing zones. Thus, the cement 185 provides a barrier to separate zone 177 from zone 179 behind the casing 180. This procedure of casing installation and cementing is repeated for each section of the wellbore 130 corresponding to each formation zone 177, 179 as the well is drilled deeper. Each subsequent casing string, such as casing 190, is set by lowering the casing 190 through the previously set casing 180. Therefore, casing 190 will have a smaller diameter than the previously set casing 180. Thus, when drilling a well, multiple casing strings 180, 190 are disposed along the wellbore 130 and cemented 185, 195 into place, thereby isolating each zone 177, 179 in the formation 175. If the zones 177, 179 are not isolated by casing 180, 190 and cement 185, 195, problems such as blowouts, lost circulation, and unwanted fracturing of the formation 175 could occur. The last section of the well to be drilled is the production borehole 132, which is in contact with the fluid reservoir 170.

Once all the casings 180, 190, have been installed and cemented 185, 195 into place, the drillstring 110 and drilling assembly 120 are removed and another assembly (not shown) is run into the wellbore 130 to make perforations through the casings 180, 190 so that hydrocarbons will flow from the formation 175 into the wellbore 130. Perforations are made through the casings 180, 190 that line hydrocarbon-bearing zones 177, 179 of the formation 175, and the cement 185, 195 prevents fluids, such as water, for example, from non-hydrocarbon bearing zones from flowing behind the casings 180, 190, and through the perforations. A production tubular (not shown) is then inserted into the wellbore 130 to carry the hydrocarbons back to the surface. The process of perforating the casings 180, 190 and inserting the production tubing is known as "completion".

Some of the perceived advantages of using lasers or other thermal technologies stem from problems encountered with the above-described conventional methods of well drilling and completion. For example, many drilling problems occur before the casing 180, 190 is run and cemented 185, 195 into place because the wellbore 130 is unsealed and unprotected. An unsealed wellbore 130 adjacent an overpressured zone enables the influx of fluids from the formation 175, which can result in pressure "kicks." Further, an unsealed wellbore 130 adjacent an underpressured zone enables the loss of drilling fluids into the surrounding formation 175, which may lead to lost circulation, formation damage, differential pressure sticking, borehole swelling, borehole fracture, and even borehole collapse. Accordingly, there is a need for a method to protect the wellbore 130, even temporarily, after a new section has been drilled until a permanent casing 180, 190 can be installed and cemented 185, 195 into place. Further, because the casings 180, 190 telescope down in size from the top of the wellbore 130 to the bottom of the wellbore 130, and the driller may not know in advance the number of pressure zones 177, 179 that will be encountered, it is difficult to predict with certainty the number of casings 180, 190 that will be required and the size of the production borehole 132. In some cases, the production borehole 132 is so small that the hydrocarbons cannot be produced fast enough to make the well economically viable. Accordingly, there is a need for a method to protect and isolate the wellbore 130 without setting intermediate casing strings that reduce the diameter of the production borehole 132.

Figure 2:
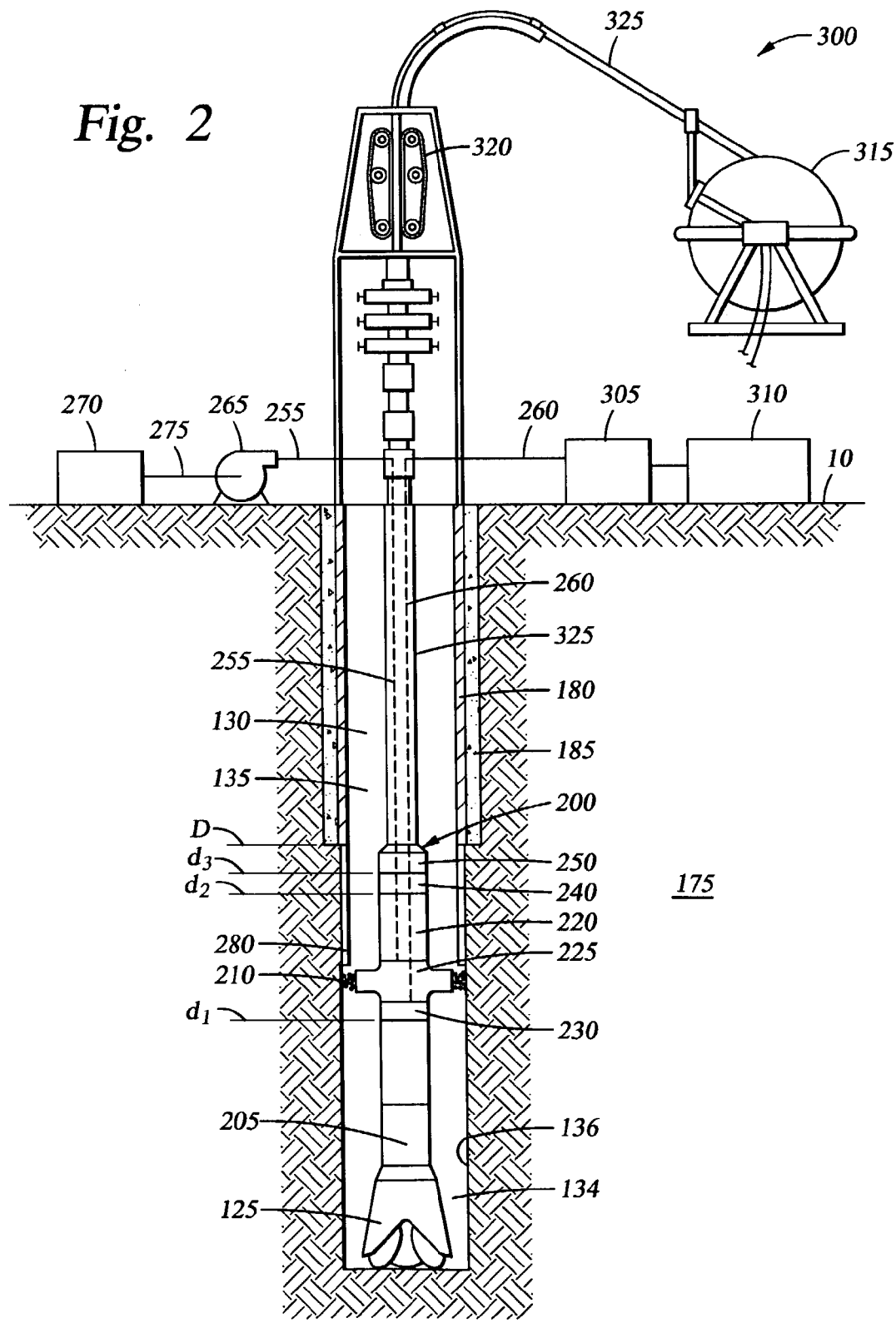
FIG. 2 is a schematic of an exemplary wellbore stabilization operation.

Referring now to FIG. 2, there is depicted a schematic of one exemplary wellbore stabilization operation that protects and isolates the wellbore 130. FIG. 2 depicts a coiled tubing drilling system 300 having a power supply 305, a surface processor 310, and a coiled tubing spool 315. An injector head unit 320 feeds and directs the coiled tubing 325, which may be either metal or composite coiled tubing, from the spool 315 downwardly into the wellbore 130. The coiled tubing 325 supports a wellbore stabilization and drilling assembly 200 within the wellbore 130 that comprises a standard drill bit 125 driven by a drill motor 205, an extruder 225, a heat source 220, and preferably a plurality of temperature sensing devices 230, 240, 250, each of which is capable of measuring the temperature of the formation 175 in its vicinity. A reservoir 270 on the surface 10 connects to a pump 265 via an inlet conduit 275, and the pump 265 connects to an exit conduit 255 that extends downwardly through the bore 322 of the coiled tubing 325 to the extruder 225. A standard wireline 260, such as a 7-conductor wireline, extends downwardly through the bore 322 of the coiled tubing 325 to conduct power from the surface power supply 305 to the wellbore stabilization and drilling assembly 200 for operating the heat source 220. The wireline 260 further conducts signals from the temperature sensing devices 230, 240, 250 to the signal processing unit 310 on the surface. It will be appreciated by those skilled in the art that the wellbore stabilization and drilling assembly 200 also contains appropriate power supply circuitry and data transmission circuitry (not shown) for operating the heat source 220 and temperature sensing devices 230, 240, 250, and for transmitting measurements made thereby to the surface for further processing.

Figure 2A:
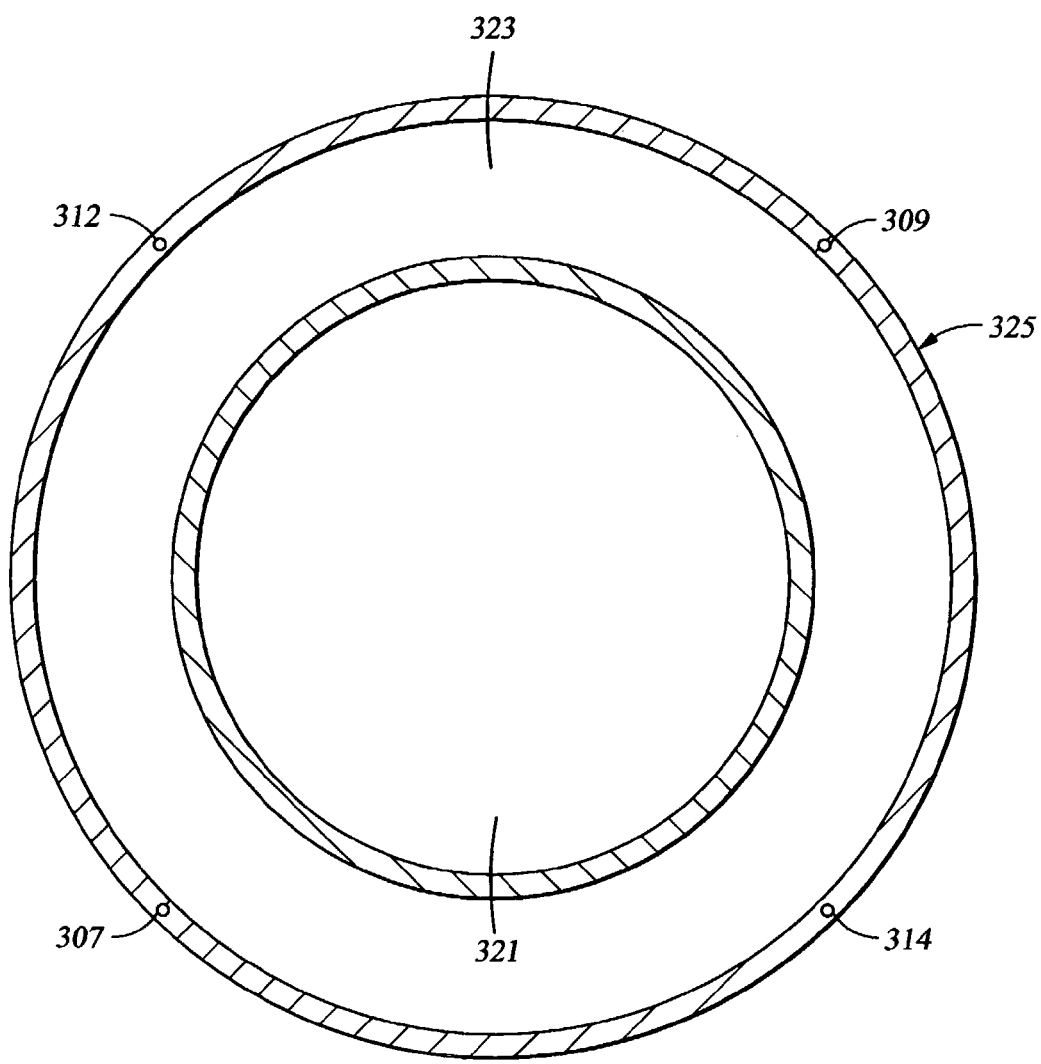
FIG. 2A is a cross-sectional end view of an exemplary multi-bore coiled tubing.

In operation, drilling fluid is pumped through the bore 322 of the coiled tubing 325 to power the drill motor 205, which in turn powers the drill bit 125. Simultaneously, the extruder 225 and the heat source 220 enable placement of a temporary liner 280 to line the wellbore 130 in sections where casings have not yet been installed, such as along the lower borehole section 134 of FIG. 2. In particular, pump 265 pumps a fusible liner material 210, such as polyethylene or polypropylene, for example, from the reservoir 270 through the exit conduit 255 and downwardly to the extruder 225, which extrudes the liner material 210 onto the wall 136 of the lower borehole section 134. The fusible liner material 210 may be provided in the form of liquid or small solid pellets, for example, or any other suitable form. As the wellbore stabilization and drilling assembly 200 reaches the lower borehole section 134, preferably the ambient temperature of the formation 175 is measured by sensor 230 at a predetermined depth D. Then, after the fusible liner material 210 is extruded onto the wall 136 of the lower borehole section 134, the heat source 220 is activated to heat the fusible liner material 210, thereby melting it. As the wellbore stabilization and drilling assembly 200 advances, the melted fusible liner material 210 is forced into the porosity of the formation 175, and as the liner material 210 cools, it creates a temporary liner 280 along the lower borehole section 134 as depicted in FIG. 2. In another embodiment, instead of pumping the liner material 210 through a separate conduit 255 extending through the coiled tubing bore 322, the coiled tubing 325 could have more than one bore. For example, as depicted in cross-section in FIG. 2A, the coiled tubing 325 could comprise two bores, such as a central fluid bore 321 and an outer annular bore 323. The drilling fluid could flow through the central bore 321 and the liner material 210 could flow through the annular bore 323, or vice versa. There are a variety of other possible configurations for pumping the liner material 210 to the extruder 225.

Thus, the heat source 220 melts the fusible liner material 210 to produce the temporary liner 280, while simultaneously heating the formation 175 in the vicinity of the heat source 220. As heat is applied to the formation 175, measurements of temperature changes in the formation 175 induced in the vicinity of the temperature sensing devices 230, 240, 250 enables the determination of thermal properties of the formation 175, as in conventional methods. In particular, as the wellbore stabilization and drilling assembly 200 moves downwardly, the temperature sensing devices 230, 240, 250, which are spacially separated, each pass depth D in the formation 175 at different times such that temperature measurements can be made at the same depth D over time to measure the time rate of decay of the temperature at depth D. Alternatively, once the formation 175 has been heated to form the temporary liner 280, the wellbore stabilization assembly 200 may be held stationary, thereby keeping sensors 230, 240, 250 stationary within the wellbore 130. Then a plurality of temperature measurements may be made at the depths d1, d2, d3 of each sensor 230, 240, 250 respectively, over time, to measure the time rate of decay of the temperature at each depth d1, d2, d3. The temperature differentials and other measurements are then used to infer thermal properties according to conventional calculations.

Figure 3:
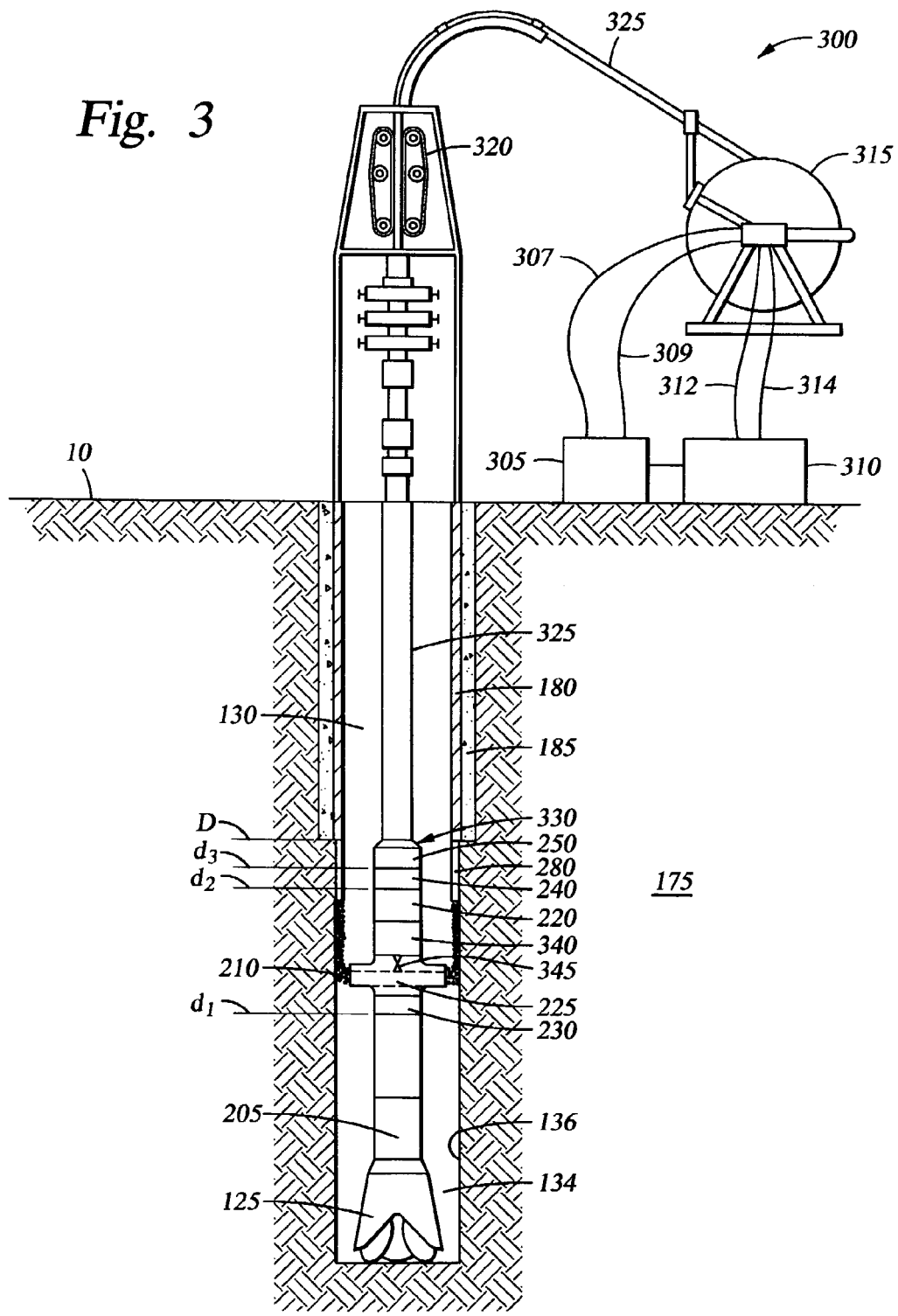
FIG. 3 is a schematic of another exemplary wellbore stabilization operation.

Referring now to FIG. 3, there is depicted a schematic of another exemplary wellbore stabilization operation. FIG. 3 depicts a coiled tubing drilling system 300 having a power supply 305, a surface processor 310, and a coiled tubing spool 315. An injector head unit 320 feeds and directs the coiled tubing 325, which is composite coiled tubing, from the spool 315 downwardly into the wellbore 130 to support a wellbore stabilization and drilling assembly 330 on its lower end. The power supply 305 may be connected by electrical conduits 307, 309 to electrical conduits in the wall of the composite coiled tubing 325. Alternatively, the power supply 305 may be connected to a wireline 260 that extends through the bore 322 of the coiled tubing 325, as depicted in FIG. 2. Further, the surface processor 310 includes data transmission conduits 312, 314 that may be connected to data transmission conduits also housed in the wall of the composite coiled tubing 325. Alternatively, the surface processor 310 may be connected to a wireline 260 that extends through the bore 322 of the coiled tubing 325, as depicted in FIG. 2.

The wellbore stabilization and drilling assembly 330 includes many of the same components as the wellbore stabilization and drilling assembly 200 of FIG. 2. However, the assembly 330 of FIG. 3 includes a downhole reservoir 340 rather than the surface reservoir 270, pump 265, and conduit 255 extending through the coiled tubing 325, as shown in FIG. 2.

In operation, drilling fluid is pumped through the bore 322 of the coiled tubing 325 to power the drill motor 205, which in turn powers the drill bit 125. Simultaneously, the extruder 225 and the heat source 220 enable placement of a temporary liner 280 to line the wellbore 130 in sections where casings have not already been installed, such as along the lower borehole section 134 of FIG. 3. To create the temporary liner 280, the fusible liner material 210 is selectively dispensed, such as via an actuatable valve 345, for example, from the downhole reservoir 340 into the extruder 225, which extrudes the liner material 210 onto the wall 136 of the lower borehole section 134. Then, after the fusible liner material 210 is extruded, the heat source 220 melts the fusible liner material 210. In an alternate embodiment, the downhole reservoir 340 may be positioned above another type of heat source (not shown), such that the fusible liner material 210 may be selectively dispensed into the heat source to be heated therewithin before being extruded. Thus, in the alternate embodiment, the extruder 225 extrudes melted liner material 210 onto the lower borehole wall 136. Once the liner material 210 is extruded and melted, then as the wellbore stabilization and drilling assembly 330 advances, it forces the melted fusible liner material 210 into the porosity of the wellbore 130 to create a temporary liner 280.

Thus, the heat source 220 or the alternate heat source (not shown) melts the fusible lining material 210 to produce a temporary liner 280, while simultaneously heating the formation 175 in the vicinity of the heat source 220. As heat is applied to the formation 175, measurements of temperature changes of the formation 175 induced in the vicinity of temperature sensing devices 230, 240, 250 enable the determination of thermal properties of the formation 175, as in conventional methods. In particular, as the wellbore stabilization and drilling assembly 330 moves downwardly, the temperature sensing devices 230, 240, 250, which are spacially separated, will each pass depth D in the formation 175 at different times such that temperature measurements can be made at the same depth D to measure the time rate of decay of the temperature at depth D. Alternatively, once the formation 175 to form the temporary liner 280, the wellbore stabilization assembly 330 can be held stationary, thereby keeping sensors 230, 240, 250 stationary within the wellbore 130. Then a plurality of temperature measurements may be made at the depths d1, d2, d3 of each sensor 230, 240, 250 respectively, over time, to measure the time rate of decay of the temperature at each depth d1, d2, d3. The temperature differentials and other measurements are then used to infer thermal properties according to conventional calculations.

The heat source 220 in the assemblies 200, 330 of FIG. 2 and FIG. 3, respectively, may comprise any source of heat, such as for example, a heat tip that reaches sufficient temperatures to melt the fusible liner material 210. In another embodiment, the heat source 220 comprises a laser as will be described in more detail hereinafter. A laser can reach temperatures capable of melting the formation 175 rock, and when the molten rock cools, a liner is formed such that no fusible liner material 210 is required.

Beyond wellbore stabilization, lasers are now being utilized for drilling. Unlike conventional drilling, in which the drilling rate is determined by the weight-on-bit (WOB), mud circulation (cuttings removal) rate, rotary speed, hydraulic horsepower, bit design and wellbore size, the rate of penetration achieved with a laser may only depend on wellbore size and delivered power. Moreover, no out-of-balance or out-of-axis turning is expected to occur with a laser-drilled wellbore, and, because a laser head does not contact the rock, there is no need to stop drilling to replace a mechanical bit.

A laser is basically a device that converts energy of some form (electrical, chemical, heat, etc.) into photons, which is electromagnetic radiation. The photons created through stimulated emission form a narrow beam of monochromatic coherent light energy that when focused into an intense beam can be used to fragment, melt or vaporize rock, depending upon the power delivered, and the operating parameters associated with pulsing the laser.

Figure 4:
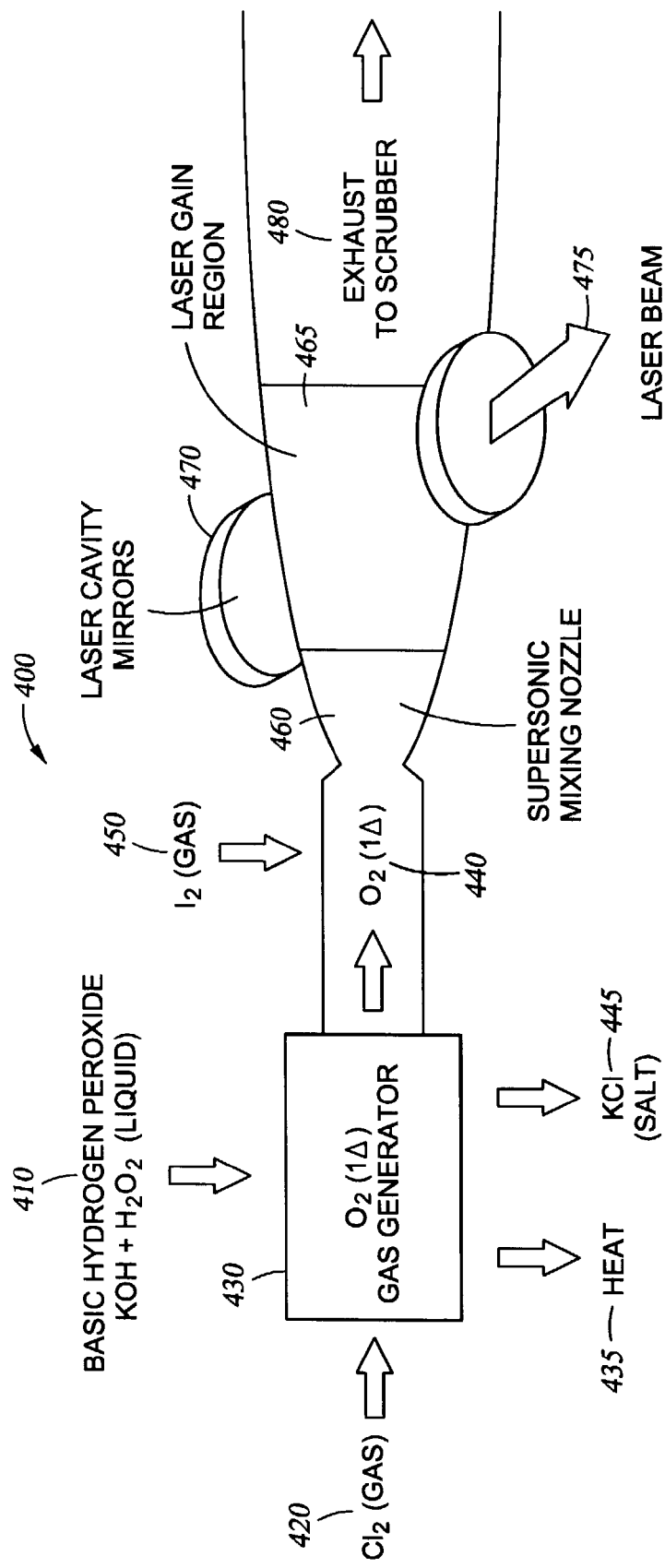
FIG. 4 is a schematic of a chemical oxygen-iodine laser (COIL)

Referring now to FIG. 4, there is shown a schematic of one embodiment of a laser that could be used for drilling a wellbore; namely a chemical oxygen-iodine laser (COIL) 400. The overall COIL process is conceptually simple. Basic hydrogen peroxide (BHP) 410 when mixed with chlorine gas 420 in a gas generator 430 produces oxygen in an excited state (called the oxygen singlet delta 440). The byproduct of this reaction is heat 435 and brine 445, which is common in the oilfield. The oxygen singlet delta 440 is combined with molecular iodine 450 in a supersonic mixing nozzle 460, which causes both the dissociation of molecular iodine to atomic iodine and produces iodine in an excited state, creating the laser gain region 465. In the laser gain region 465, laser cavity mirrors 470 stimulate excited iodine to form atomic iodine, releasing photons, or "packets" of light energy that is the laser beam 475. The exhaust gases are scrubbed in a scrubber 480 to remove any residual iodine and chlorine.

While a COIL has been described as one type of laser that could be used for purposes of laser drilling, a number of alternate laser systems could also be used, including hydrogen fluoride (HF), deuterium fluoride (DF), carbon dioxide ($CO_2$), carbon monoxide (CO), free electron laser (FEL), neodymium:yttrium aluminum garnet (Nd:YAG), and krypton fluoride excimer (KrF (excimer)) lasers, for example. Lasers can operate in continuous-wave (CW), pulsed, and repetitively pulsed (RP) modes. The main energetic parameter for a CW laser is the output power, for a pulsed laser the output energy, and for a RP laser the average power and pulsed energy. Each of these lasers operates at a specific wavelength range, except for the FEL, which may be tuned to virtually any wavelength in continuous wave (CW) mode.

Figure 5:
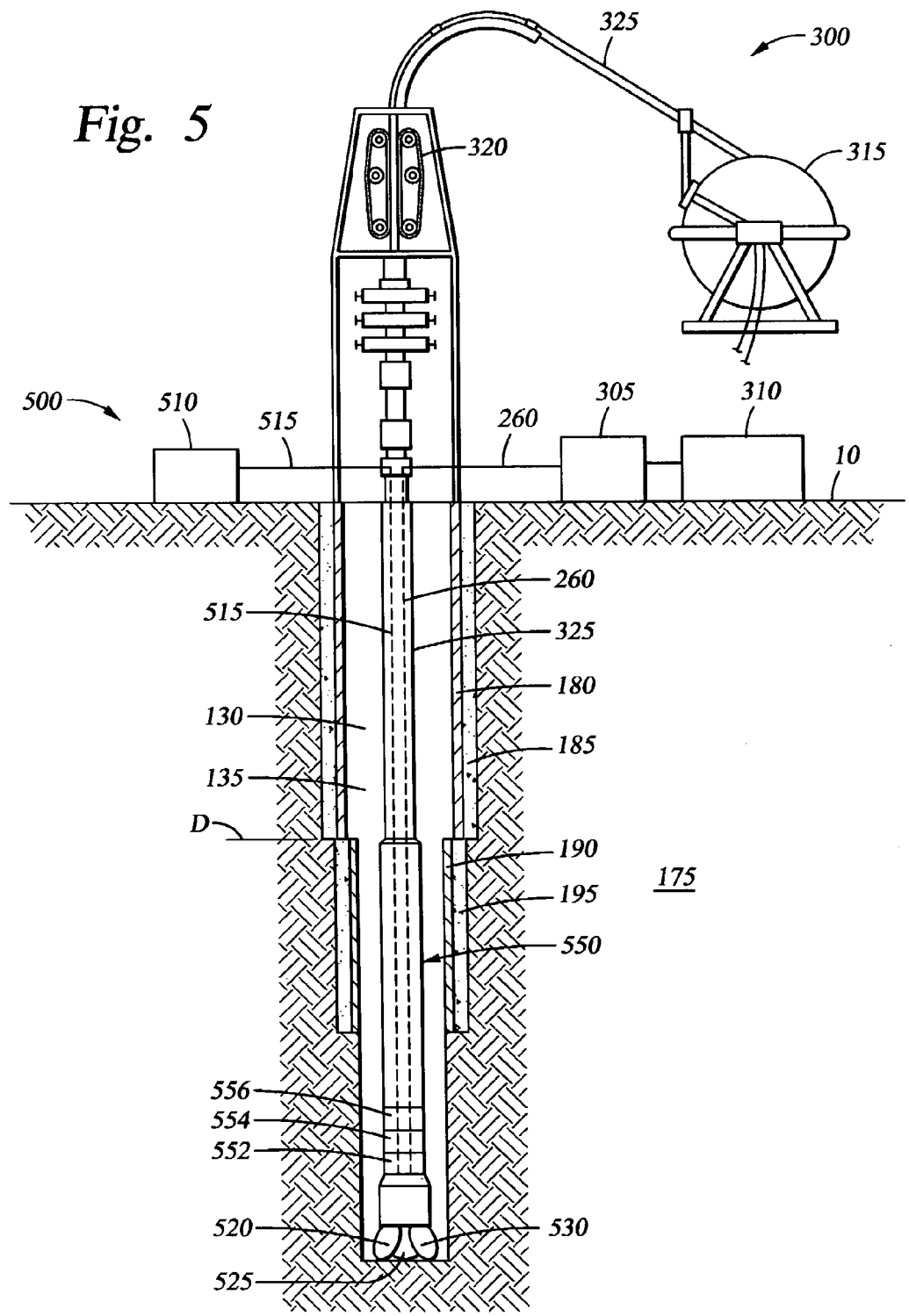
FIG. 5 is a schematic of an exemplary laser drilling system.

FIG. 5 schematically depicts one embodiment of a laser drilling system 500 as it is drilling a wellbore 130 into a formation 175. The laser drilling system 500 comprises a laser 510 on the surface, such as a FEL or COIL, connected to one or more fiber optic elements 515 comprising a bundle that extends downwardly through a coiled tubing drillstring 325 and connects to a series of lenses 520, 525, 530 on the lower end of a laser drilling assembly 550. In an alternate embodiment, a smaller laser, such as a diode laser (not shown), is small enough to fit within the wellbore 130, such as at the lower end of the laser drilling assembly 550, thereby eliminating the need for fiber optic elements 515.

In FIG. 5, the laser drilling assembly 550 is suspended within the wellbore 130 by a coiled tubing system 300 having a power supply 305, a surface processor 310, and a coiled tubing spool 315. An injector head unit 320 feeds and directs the coiled tubing 325, which may be either metal or composite coiled tubing, from the spool 315 downwardly into the wellbore 130 to support the laser drilling assembly 550. The power supply 305 is shown connected to a wireline 260 that extends through the bore 322 of the coiled tubing 325 and conducts power from the power supply 305 to the laser drilling assembly 550. Alternatively, the power supply 305 may be connected to electrical conduits in the wall of the coiled tubing 325. Further, the surface processor 310 connects to the wireline 260 to form a bi-directional telemetry system. In particular, the wireline 260 conducts data signals from several temperature sensors 552, 554 and 556 disposed on the laser drilling assembly 550 to the surface processor 310, and the surface processor 310 may also generate command signals that are conducted downhole via the wireline 260 to the laser drilling assembly 550 to alter the laser drilling operations. Alternatively, instead of the wireline 260, the surface processor 310 may be connected to data transmission conduits housed in the wall of the coiled tubing 325 to form the bi-directional telemetry system.

In operation, the laser drilling system 500 transfers light energy from the laser 510 on the surface, down the one or more fiber optic elements 515 to the series of lenses 520, 525, 530. The lenses 520, 525, 530 direct a laser beam to cut the rock and extend the wellbore 130. As the laser 510 transfers light energy downhole, heat is produced that will enable time rate of decay temperature measurements to be taken by the temperature sensors 552, 554, 556. In particular, as the laser drilling assembly 550 moves downwardly to extend the wellbore 130, the temperature sensors 552, 554, 556, which are spacially separated, will pass a depth D in the formation 175 at different times such that temperature measurements can be made at the same depth D over time.

Thus, a temperature differential can be determined from which thermal properties can be inferred by conventional methods.

One of the primary benefits of making these real-time thermal property determinations is to enhance laser drilling operations. Thermal properties, such as thermal diffusivity, are especially valuable for determining properties of the formation rock. For example, the laser 510 utilized for drilling will have different pulse rates and different preferred operating parameters, such as how long and how often to pulse the laser, for example, depending upon the type of formation rock. In some cases, the same amount of laser energy will melt one type of rock while it will vaporize another. Thus, real-time information about formation properties enables improvements to be made in the laser drilling process. In particular, as drilling progresses, temperature measurements are made via temperature sensors 552, 554, 556 disposed on the drilling assembly 550. The wireline 260 conducts signals from the temperature sensors 552, 554, and 556 to the surface processor 310 where the data is processed to determine thermal properties of the formation 175. Then, various parameters of the laser 510, such as the pulse rate, for example, may be adjusted depending upon the characteristics of the formation 175.

Figure 6:
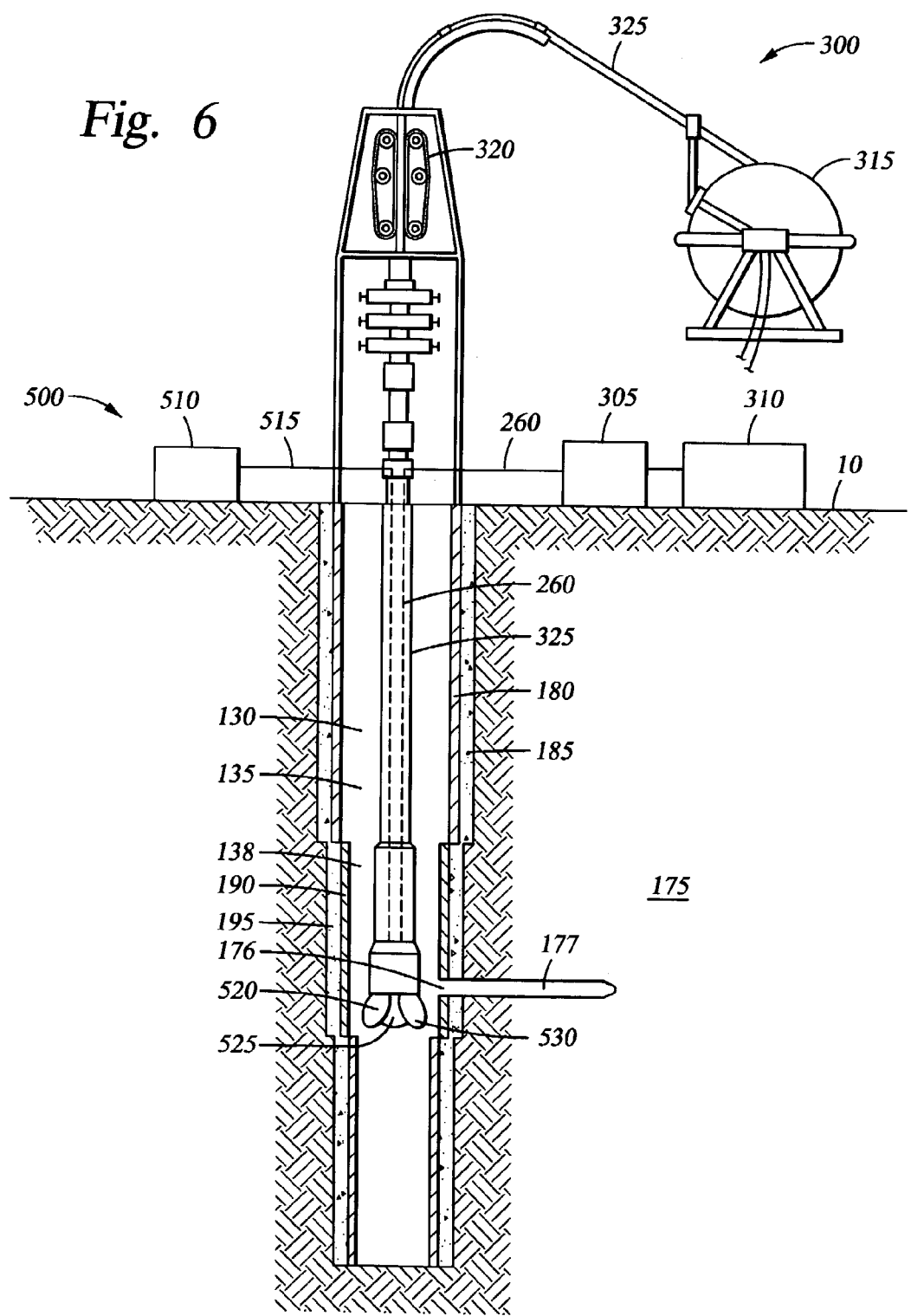
FIG. 6 is a schematic of an exemplary laser perforating system.

FIG. 6 schematically depicts the laser 510, the one or more fiber optic elements 515, and the lenses 520, 525, 530 being utilized to perforate casing 190 in the middle section 138 of the wellbore 130. In this configuration, the laser 510 transfers light energy down the fiber optic elements 515 to the series of lenses 520, 525, 530. The lenses 520, 525, 530 then direct a laser beam to perforate the casing 190, cement 195, and formation 175 to form a perforation 176.

In another embodiment, since light energy from a laser, such as laser 510, can be conducted along a fiber optic element 515 for short distances, the lenses 520, 525, 530 can be eliminated. In this embodiment, the laser 510 transfers light energy down the one or more fiber optic elements 515, and the ends of the fiber optic elements 515 are positioned to direct a laser beam to perforate the casing 190, cement 195, and formation 175. It would also be possible to point the end of each one of the fiber optic elements 515 to various different positions along the length of the casing 190 to form multiple perforations 176 simultaneously. For example, assuming there are ten (10) fiber optic elements 515 bundled to a single laser source 510, the end of each one of the fiber optic elements 515 may be pointed to a different location along the casing 190. Then light energy from the laser 510 may be conducted to the ends of the individual fiber optic elements 515 in sequence to create ten perforations 176. In particular, since each pulse of the laser 510 lasts only briefly when perforating so as to spall rather than melt the rock, the light energy can be conducted (pulsed) to each fiber element 515 in sequence at a rapid pace to generate the ten perforations 176, with the sequence returning to the first perforation in time for the next pulse. This sequence would be repeated multiple times to create completed perforations along the casing 190 length. The laser 510 could be located on the surface as shown in FIG. 6, or alternatively, the laser 510 could be disposed within the wellbore 130. It may also be possible to form and extend a perforation tunnel 177 using a fiber optic element 515 by projecting the element 515 out into the perforation 176 and pulsing the laser 510 to continue spalling the rock and form a progressively longer perforation tunnel 177.

A properly pulsed laser 510 may create fewer but higher quality perforations 176 as compared to conventional perforating methods. In particular, using a conventional perforator that dispenses shape charges, a plurality of perforations can be created in a short period of time. However, many of these perforations do not extend deep enough into the formation, or they may be blocked with casing and rock debris that is forced into the perforation and surrounding formation by the shape charge, thereby reducing the effective produceability of the formation. Therefore, although a large number of perforations can be created using a conventional perforator, few of the perforations will produce. For example, if 50 feet of casing length is perforated, approximately only 5 feet of perforations may actually produce. In contrast, the perforations 176 created with a laser 510 do not get blocked with debris and can be extended to form a tunnel 177 in the formation 175 as needed. In fact, as reported in "Temperature Induced by High Power Lasers: Effects on Reservoir Rock Strength and Mechanical Properties", SPE/ISRM 78154, data indicates that in many cases the effective permeability of the rock around the tunnel 177 is actually increased relative to that of the virgin formation 175. Therefore, it is possible for a majority of the laser-created perforations 176 to produce.

Once again, heat is generated in the formation 175 as a result of the laser perforating operation performed by any of the above-described methods. Temperature probes can be installed in a perforation tunnel 177 to measure the temperature relaxation at one or more positions within the perforation tunnel 177 over time. In one embodiment, the temperature probes comprise a fiber optic element 515, which, as known in the art, can make distributed measurements along the length of the fiber. The fiber optic element 515 may be part of the bundle connected to the laser 510, or it may be a separate fiber optic element connected to another laser. Accordingly, since a fiber optic element 515 can be used to spall rock to form perforations 176 and tunnels 177, and can also be used to take distributed temperature measurements, the same laser 510 and fiber optic elements 515 can be used for both purposes. In such a case, the laser 510 would be operated in one mode to form the perforations 176 and tunnels 177 and in a different mode to make temperature measurements.

In more detail, to make distributed temperature measurements using a fiber optic element 515, the laser 510 is operated to pulse light energy down the fiber optic element 515. Temperature measurements can be made at each point along the length of the fiber 515. Most distributed temperature sensing systems utilizing fiber optic elements 515 rely on Optical Time Domain Reflectometry (OTDR), which is known in the art, to determine the spatial position of an individual measurement. OTDR is a standard method of determining losses along the length of an optical fiber 515. The time it takes for the reflective light to return to the source indicates the precise position along the fiber 515 where the measurement is being taken. The characteristics of the reflective light are analyzed using known techniques, such as Raman backscattering, to determine the temperature at that precise position. Thus, for each pulse of the laser 510, the operator can obtain reflective light measurements at different times corresponding to different positions along the fiber optic element 515. The operator can then pulse the laser 510 again and repeat the measurement sequence at each position along the fiber optic element 515, and so on. This will provide a number of temperature measurements at each position such that temperature differentials can be determined from which thermal properties can be inferred by conventional methods. Although the length of the fiber optic element 515 is located at approximately the same depth in the formation 175 when disposed within a perforation tunnel 177, distributed temperature measurements along the length of the fiber 515 are valuable for determining the properties of the formation 175 with greater accuracy, and for determining the required depth of the perforation tunnels 177 to engage formation zones containing the most hydrocarbons.

One of the primary benefits of making real-time thermal property determinations is to enhance laser perforating operations based upon the characteristics of the rock comprising the formation 175. For example, as previously described, temperature measurements may be made within a perforation tunnel 177 via a temperature probe (not shown) or a fiber optic element 515, and the temperature signals may then be transmitted to the surface processor 310 to determine thermal properties of the formation 175. Then, various parameters of the laser 510, such as the pulse rate, intensity, and duration, can be adjusted based upon the real-time determination of thermal properties of the formation 175, thereby improving the laser perforating operation.

Thus, the preferred embodiments of the present invention take advantage of the heat from a thermal drilling, wellbore stabilization, or perforating process to perform thermal measurements. The thermal measurements may be performed simultaneously or near simultaneously with the drilling operations. The sensors thus provide in situ temperature measurements that permit the computation of thermal properties of the formation as described in the earlier '128 patent, the '227 patent and the '969 patent to Smith, Jr.

While preferred embodiments of the present invention have been shown and described, modifications thereof can be made by one skilled in the art without departing from the spirit or teaching of this invention. For example, a fiber optic element and laser could be utilized to take distributed temperature measurements along the wellbore during thermal drilling or wellbore stabilization operations in addition to perforating. Thus, the embodiments described herein are exemplary only and are not limiting. Many variations and modifications of the methods and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A method for determining the thermal properties of a downhole formation, comprising:
    cutting and heating the formation with a laser beam adjacent a selected depth level within a wellbore extending into the formation;
    measuring a first temperature of the formation at the selected depth level at a first time after heating the formation;
    measuring a second temperature of the formation at the selected depth level at a second time after heating the formation; and
    combining the temperature measurements to derive an indication of the thermal properties of the formation according to known mathematical relationships.

2. The method of claim 1 further comprising measuring the ambient temperature of the formation at the selected depth level.

3. The method of claim 1 wherein the laser beam is used for measuring the temperatures.

4. The method of claim 1 wherein cutting the formation comprises transferring light energy from a laser to at least one component that directs the laser beam toward the formation.

5. The method of claim 4 wherein the at least one component is a series of lenses.

6. The method of claim 5 wherein the light energy is transferred from the laser through at least one fiber optic element to the lenses.

7. The method of claim 4 wherein the at least one component is one ormore fiber optic elements.

8. The method of claim 4 wherein the laser is disposed within the wellbore.

9. The method of claim 1 wherein cutting the formation comprises extending the wellbore.

10. The method of claim 1 wherein cutting the formation comprises perforating through a casing lining the wellbore.

11. The method of claim 10 further comprising forming a perforation tunnel in the formation.

12. The method of claim 11 wherein measuring the temperatures comprises inserting a temperature probe into the tunnel.

13. The method of claim 12 wherein the temperature probe comprises a fiber optic element.

14. The method of claim 13 wherein measuring the temperatures comprises making distributed temperature measurements along the fiber optic element.

15. The method of claim 11 further comprising extending the tunnel by transferring light energy from a laser to a fiber optic element disposed within the tunnel.

16. The method of claim 15 wherein measuring the first and second temperatures comprises making distributed temperature measurements along the fiber optic element.

17. The method of claim 1 wherein measuring the temperatures comprises spacing at least two temperature sensors axially with respect to the wellbore and moving each of the temperature sensors to the selected depth level.

18. The method of claim 17 wherein the at least two temperature sensors comprise a fiber optic element.

19. The method of claim 1 wherein measuring the temperatures comprises positioning a temperature sensor at the selected depth level and maintaining the sensor at the selected depth level while measuring the first temperature and the second temperature.

20. The method of claim 19 wherein the temperature sensor comprises a fiber optic element.

21. The method of claim 1 wherein the thermal properties of the formation comprise one or more of the following: thermal conductivity, thermal diffusivity and specific heat.

22. The method of claim 1 further comprising altering the operation of the laser beam based on the thermal properties of the formation.

* * * * *

UNITED STATES PATENT AND TRADEMARK OFFICE
CERTIFICATE OF CORRECTION

PATENT NO. : 7,086,484 B2
APPLICATION NO. : 10/457645
DATED : August 8, 2006
INVENTOR(S) : Harry D. Smith, Jr.

It is certified that error appears in the above-identified patent and that said Letters Patent is hereby corrected as shown below:

In Claim 7, in column 14, line 13, replace "ormore" with --or more--.

Signed and Sealed this

Fourteenth Day of November, 2006

JON W. DUDAS
*Director of the United States Patent and Trademark Office*